(12) United States Patent
Girgis (10) Patent No.: US 11,559,632 B2
(45) Date of Patent: Jan. 24, 2023

(54) PASSIVE SAFETY NEEDLE SHIELD (71) Applicant: Embecta Corp., Andover, MA (US)

(72) Inventor: Peter Aziz Girgis, East Brunswick, NJ (US)

(73) Assignee: Embecta Corp., Andover, MA (US)

( * ) Notice: Subject to any disclaimer, the term of this patent is extended or adjusted under 35 U.S.C. 154(b) by 368 days.

(21) Appl. No.: 16/498,559

(22) PCT Filed: Apr. 19, 2018

(86) PCT No.: PCT/US2018/028394
§ 371 (c)(1),
(2) Date: Sep. 27, 2019

(87) PCT Pub. No.: WO2018/195326
PCT Pub. Date: Oct. 25, 2018

(65) Prior Publication Data
US 2020/0046912 A1 Feb. 13, 2020

Related U.S. Application Data

(60) Provisional application No. 62/488,006, filed on Apr. 20, 2017.

(51) Int. Cl.
*A61M 5/32* (2006.01)
*A61M 5/50* (2006.01)
(52) U.S. Cl.
CPC ............ *A61M 5/3275* (2013.01); *A61M 5/50* (2013.01); *A61M 2005/3249* (2013.01); *A61M 2005/3267* (2013.01)

(58) Field of Classification Search
CPC .................... A61M 2005/3267; A61M 5/3275
See application file for complete search history.

(56) References Cited

U.S. PATENT DOCUMENTS

| 4,892,521 | A | 1/1990 | Laico et al. |
| 4,955,866 | A | 9/1990 | Corey |
| 5,078,697 | A | 1/1992 | Rammler |
| 5,250,031 | A | 10/1993 | Kaplan et al. |
| 5,344,408 | A | 9/1994 | Partika |

(Continued)

FOREIGN PATENT DOCUMENTS

| CN | 1449845 A | 10/2003 |
| CN | 1878584 A | 12/2006 |

(Continued)

*Primary Examiner* — Deanna K Hall
(74) *Attorney, Agent, or Firm* — Greenberg Traurig, LLP; David J. Dykeman; Roman Fayerberg (57) ABSTRACT

A passive safety needle shield (300) is provided. The needle shield comprises a base (302) fixed to a proximal end of a needle, and an enclosure housing (304) initially disposed at a distal end of the needle, and enclosing the end of the needle. A hinged arm (306) connects the base (302) and the enclosure housing (304). The enclosure housing (304) is slidable along the needle length, and the hinged arm (306) flexes to permit the enclosure housing (304) to move along the needle as the needle is inserted into a user, thereby hiding the needle end, and providing support to the needle to avoid bends or buckles in the needle. The hinged arm (306) is biases in the initial position so that the enclosure housing (304) returns to the end of the needle as the needle is withdrawn.

8 Claims, 11 Drawing Sheets

(56) References Cited

U.S. PATENT DOCUMENTS

| | | | |
|---|---|---|---|
| 5,697,907 A | 12/1997 | Gaba | |
| 2002/0004650 A1 | 1/2002 | Kuracina et al. | |
| 2003/0181871 A1 | 9/2003 | Wilkinson et al. | |
| 2003/0220587 A1* | 11/2003 | Swenson | A61M 25/0625 600/576 |
| 2009/0131876 A1* | 5/2009 | Coyne | A61M 5/3275 604/198 |
| 2013/0030376 A1* | 1/2013 | Doyle | A61M 5/3245 604/198 |
| 2016/0228672 A1 | 8/2016 | Imai et al. | |

FOREIGN PATENT DOCUMENTS

| | | |
|---|---|---|
| CN | 201519342 U | 7/2010 |
| CN | 103945883 A | 7/2014 |
| JP | 2003088587 A | 3/2003 |
| JP | 2007511285 A | 5/2007 |
| JP | 2009183738 A | 8/2009 |
| JP | 2014522707 A | 9/2014 |
| WO | 2007099367 A1 | 9/2007 |

* cited by examiner

PASSIVE SAFETY NEEDLE SHIELD

PRIORITY CLAIM

This application is a National Stage entry of PCT application number PCT/US2018/028394, filed Apr. 19, 2018, which claims the benefit under 35 U.S.C. § 119(e) of U.S. Provisional Application No. 62/488,006 filed Apr. 20, 2017, the entire contents of which are hereby incorporated by reference.

FIELD OF THE INVENTION

The present invention is directed to safety devices for needles, and in particular to a novel needle shield.

BACKGROUND OF THE INVENTION

Figure 1:
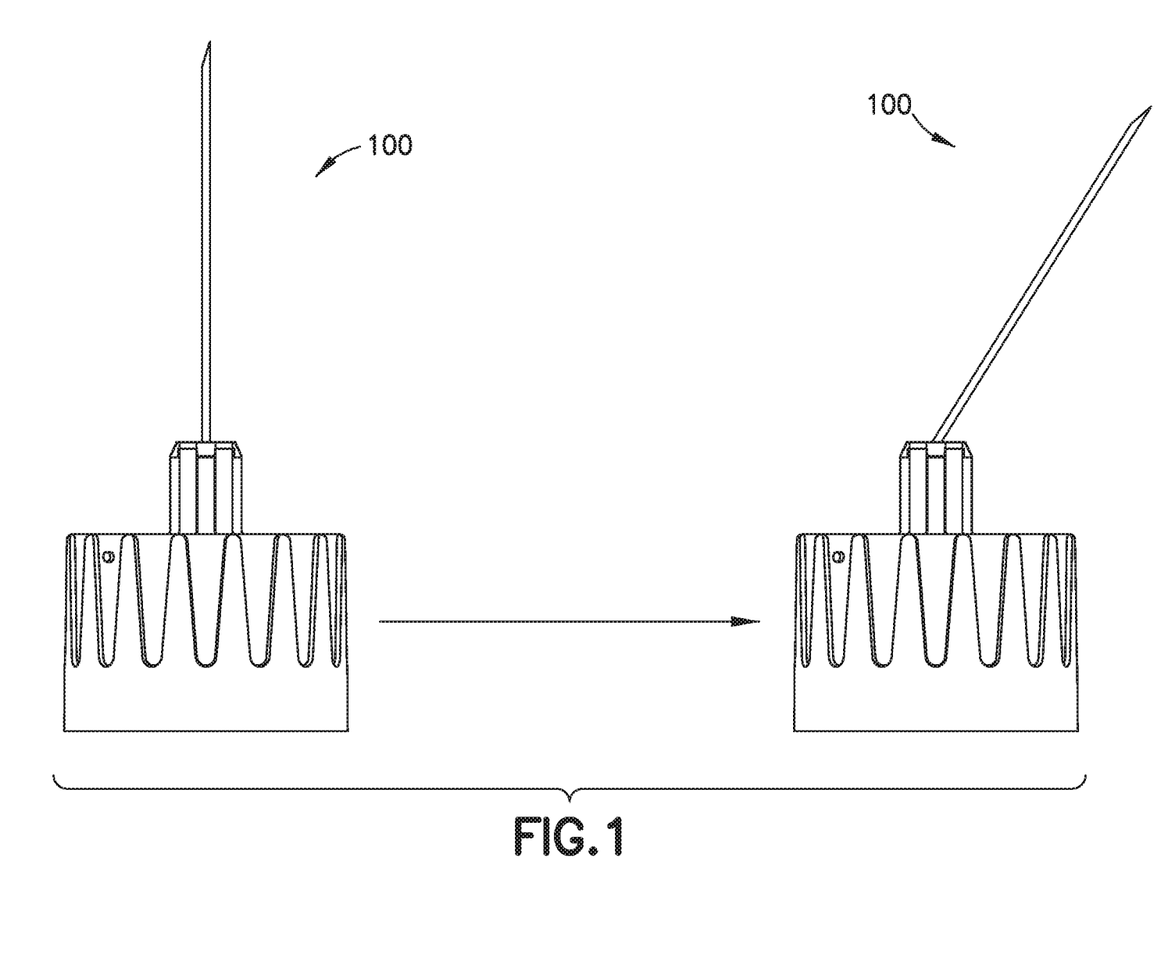
FIG. 1 illustrates a pen needle hub bending due to insertion force.

Safety is an important consideration in the manufacture of needles, particularly for medical use. Another consideration is comfort level, or reducing the pain associated with using a needle. Often a small gauge needle is used for small dose deliveries of medication in order to minimize discomfort. However, smaller gauge needles are more prone to bending, buckling and kinking during use due if the insertion force is not coaxial with the needle. FIG. 1, for example, illustrates a small gauge pen needle 100 for attachment to a pen injector. As shown, during use the thin needle may become bent or kinked. Accordingly, there is a need to prevent small gauge needles from bending during use. Most existing safety products for needles require active safety, where the user would have to physically activate the safety mechanism. Embodiments of the present invention, as described herein function on a passive safety mechanism so that there is preferably no manual activation by the user.

Figure 2:
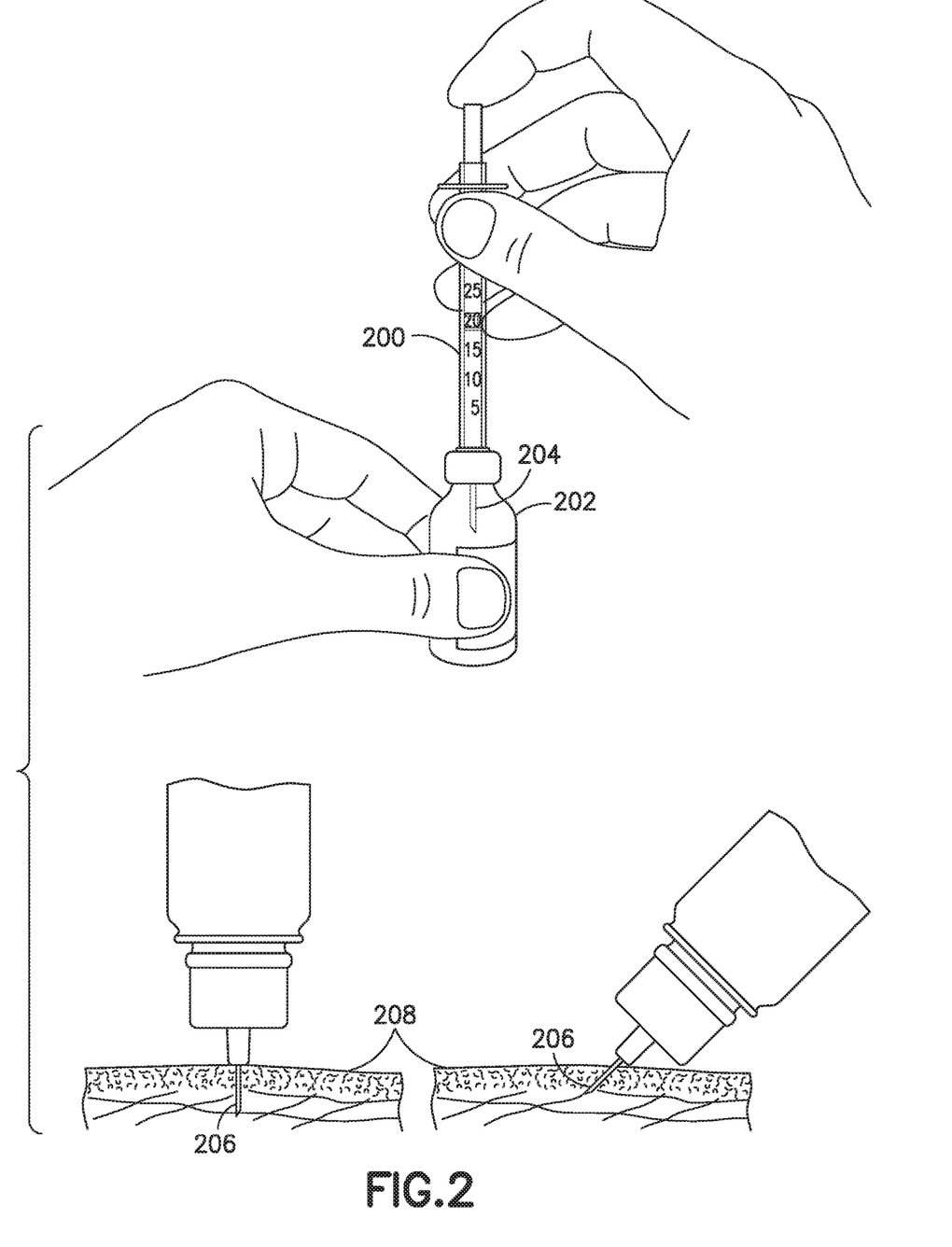
FIG. 2 illustrates a syringe being filled and a pen needle being inserted into skin.

In certain situations, as illustrated in FIG. 2, such as filling a syringe 200 from a vial 202 through a needle 204, or inserting a needle 206 into the skin 208, the orientation of the needle 206 is important. In these situations it would be helpful to provide a mechanism to increase the likelihood of inserting the needle at a desired angle, and decreasing the likelihood of needle bending. Finally, some patients wish to not see the needle penetrating their skin.

SUMMARY OF THE INVENTION

Exemplary embodiments of the present invention overcome the deficiencies discussed above, and provide additional benefits by providing a retraction mechanism and needle enclosure to displace the load on a needle and guide the needle during injection to help prevent bending and/or buckling. Additional embodiments prevent a needle from being used more than once by locking when the retraction mechanism returns to the pre-injection state. Embodiments of the present invention also address the preference of users to not see a needle enter their skin by enclosing the needle so that the user does not see the needle penetrating the skin.

BRIEF DESCRIPTION OF THE DRAWING FIGURES

Further details, features and advantages of designs of the invention result from the following description of embodiment examples in reference to the associated drawings.

Throughout the drawings, like reference numbers should be understood to represent like elements, features and structures.

DETAILED DESCRIPTION OF THE INVENTION

Figure 3A:
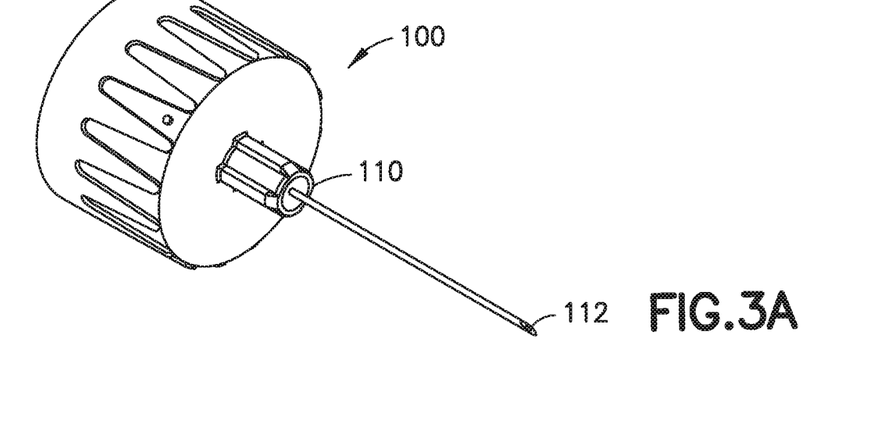
FIG. 3 illustrates a needle shield according to a first exemplary embodiment of the present invention.
Figures 3B, 3C:
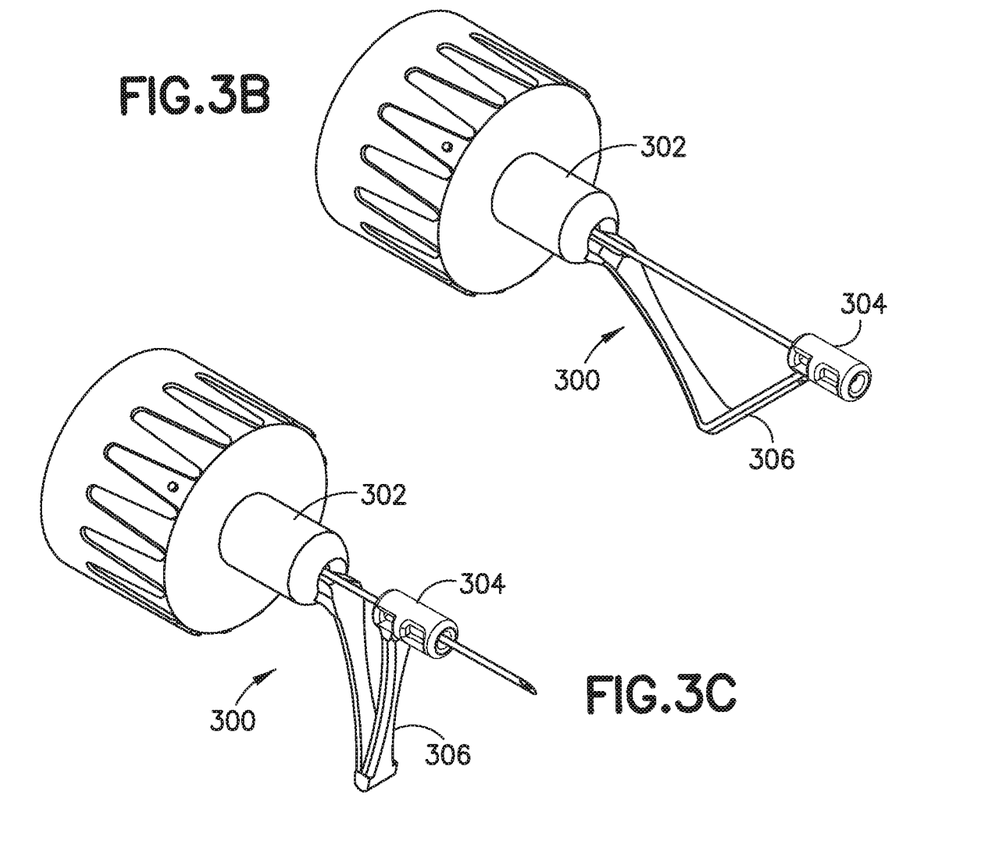

An exemplary embodiments of the present invention is illustrated in FIG. 3A-3C. FIG. 3A shows a standard pen needle for which exemplary embodiments of the present invention are useful. FIGS. 3B-3C illustrate a needle shield 300 that is added to a pen needle 100 to form an auto-retractable mechanism. As initially configured, the needle shield 300 is connected to the post 110 of the pen needle 100 at a base 302 of the needle shield 300. The end of the needle 112 is contained within an enclosure housing 304. Base 302 and enclosure housing 304 are connected by a hinged arm 306. The needle shield 300 is preferably formed of a preloaded plastic mold, such as polypropylene or the like. As shown in FIG. 3B, in the initial state, the needle end 112 is hidden within the enclosure housing 304. When the needle is inserted, the enclosure housing 304 slides down the needle towards needle post 110 as the needle penetrates the skin. The hinged arm 306 bends to accommodate this sliding motion. Then, as the patient pulls the needle out, elastic force of the hinged arm 306 pushes the enclosure housing 304 back to the end of the needle. Accordingly, the needle tip advantageously remains hidden in enclosure housing 304 to prevent accidental needle sticks and to provide comfort to patients who do not wish to see the needle penetration. The hinged arm 306 and enclosure housing 204 also combine to displace the buckling load off of the needle to prevent it from bending during use, in addition to guiding it in a straighter line through the enclosure housing.

Embodiments of the invention may advantageously be integrated with any injection product and provides a single-sided patient end safety that hides needle exposure throughout the entirety of the injection process.

The needle shield 300 is preferably formed from a preloaded plastic mold that converts preloaded potential energy into kinetic energy when force is applied to it during the skin penetration. This converted energy allows the shield to auto-retract into its original position to prevent any accidental needle sticks once the user pulls out the needle. Additionally, an auto-locking mechanism may be incorporated into the device to prevent re-use of needles on which the shield 300 is installed. The auto-locking mechanism advantageously activates once the device is retracted to its original position after a first insertion to prevent reuse and contamination.

Figure 4:
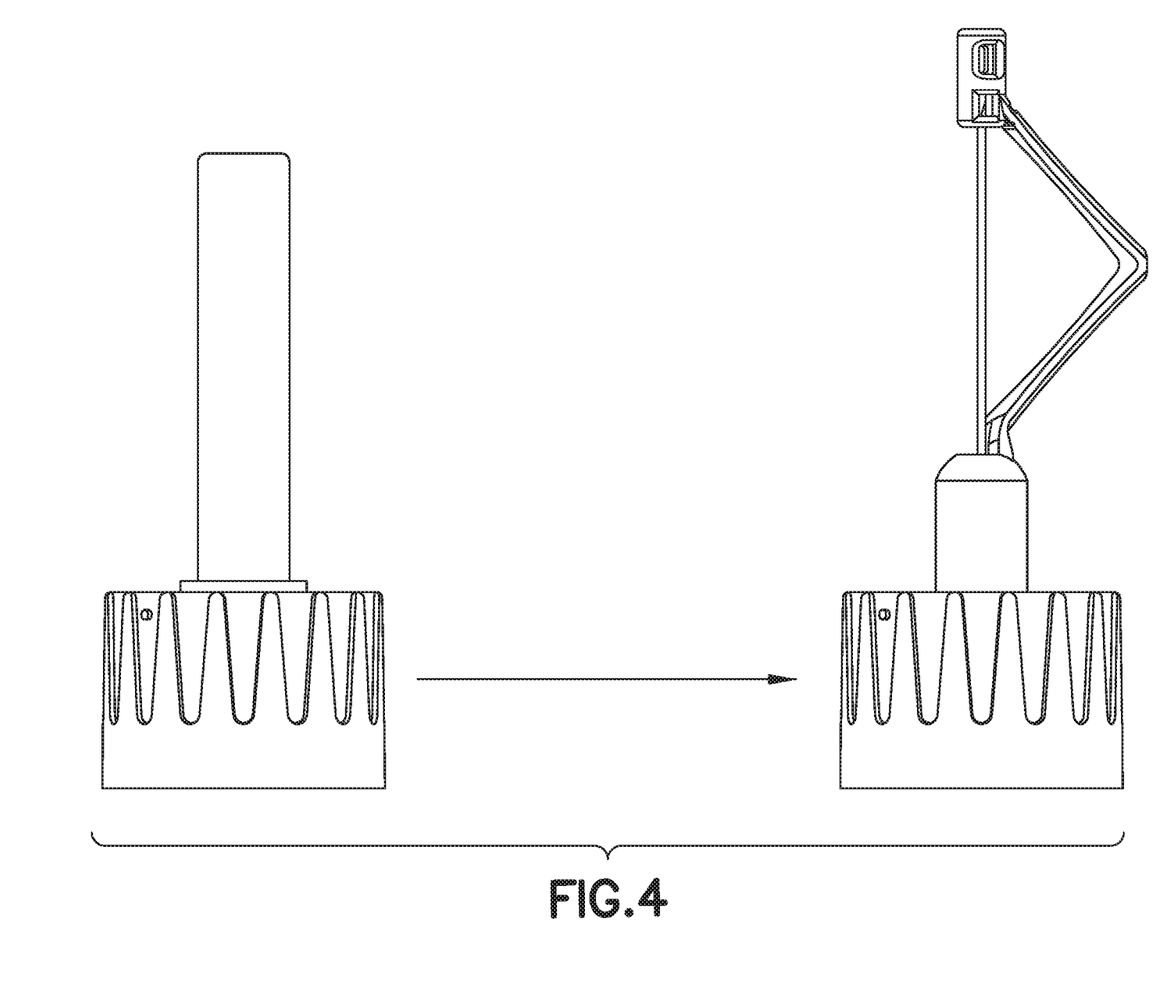
FIG. 4 illustrates the needle shield of FIG. 3 as a replacement for a conventional needle shield.

FIG. 4 illustrates a conventional pen needle 400 with a conventional needle shield 402, and also a pen needle 400 with an embodiment of the present invention 404 replacing the conventional shield 402.

Figures 5, 6, 7:
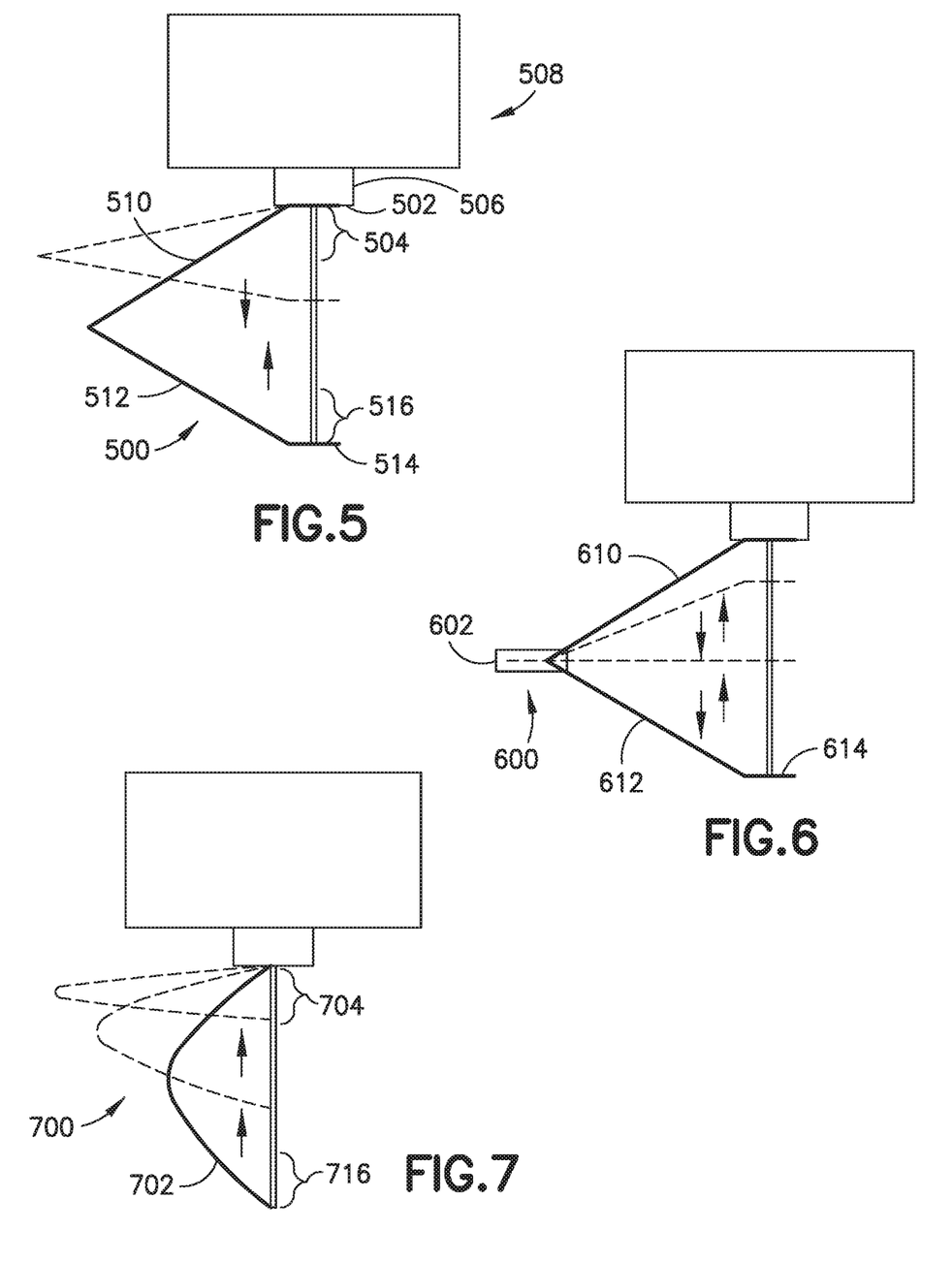
FIG. 5 illustrates a second exemplary embodiment of the invention.
FIG. 6 illustrates a third exemplary embodiment of the invention.
FIG. 7 illustrates a fourth exemplary embodiment of the invention.

Additional exemplary embodiments of the invention are illustrated in FIGS. 5-7, to demonstrate the various changes and modifications may be made to the first embodiment described above without departing from the scope and spirit of the invention. Each of these embodiments are illustrated in use with a pen needle, but those of ordinary skill in the art will readily appreciate that embodiments of the invention may be utilized with any needle. Device 500 comprises a connecting member 502 that is fixed to a proximal end of the needle 504. The connecting member 502 may be fixed to the needle by way of connection to the post 506 of the pen needle hub 508, or by direct attachment to the proximal end of the needle 504, or by any other suitable means. A first arm 510 is hingedly connected to the connecting member 502, and extends axially away from the needle as illustrated. The first arm 510 is hinged at its other end to a second arm 512. The second arm 512 is hinged at its other end to a movable member 514. The movable member 514 is slidably attached to the needle. The connecting member 502, first arm 510, second arm 512, and movable member 514 make up the protective shield 500. The shield 500 is biased in the extended position, so that it contracts during injection, and extends again as the needle is withdrawn. The movable member 514 preferably contacts the skin during needle insertion and provides a guide for the needle, improving insertion performance. The movable member 514 preferably encapsulates the distal end of the needle 516 to provide protection from accidental sticks prior to and after use, and if desired a locking mechanism (not shown) can be incorporated to lock the device and prevent a second use.

Needle shield 600 is illustrated in FIG. 6. Needle shield 600 is substantially similar to the prior described embodiment 500, but includes a bias housing 602 between the first arm 610 and second arm 612 to provide movement of the second arm 612 in and out within the bias housing 602 as the movable member 614 slides along the needle length.

Needle shield 700 is illustrated in FIG. 7. Needle shield 700 provides a single curved arm 702 fixed at a proximal end of the needle 704, and connected slidably to the distal end of the needle 716.

Figure 8:
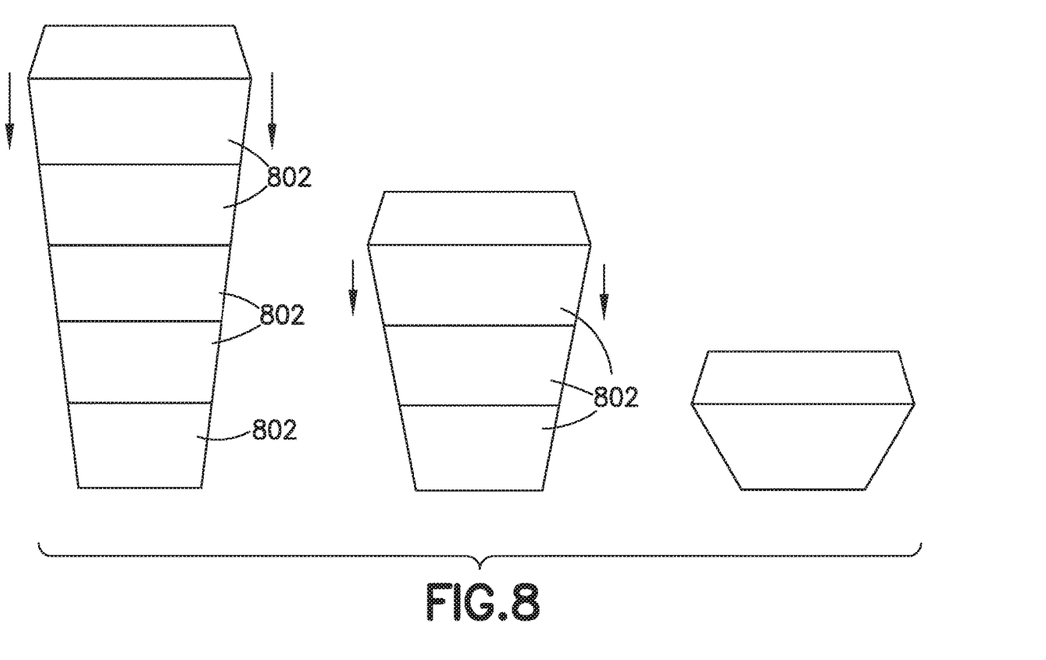
FIG. 8 is a side view illustrating a telescoping exemplary embodiment of the invention.
Figure 9:
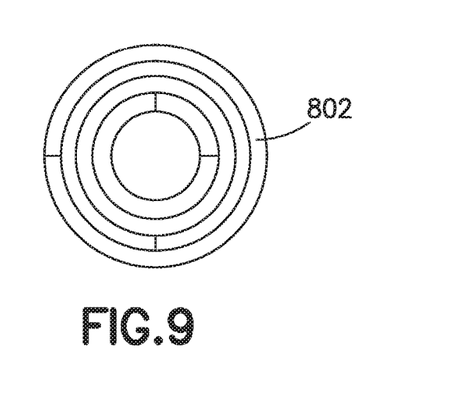
FIG. 9 is a top view of the embodiment of FIG. 8.
Figure 10:
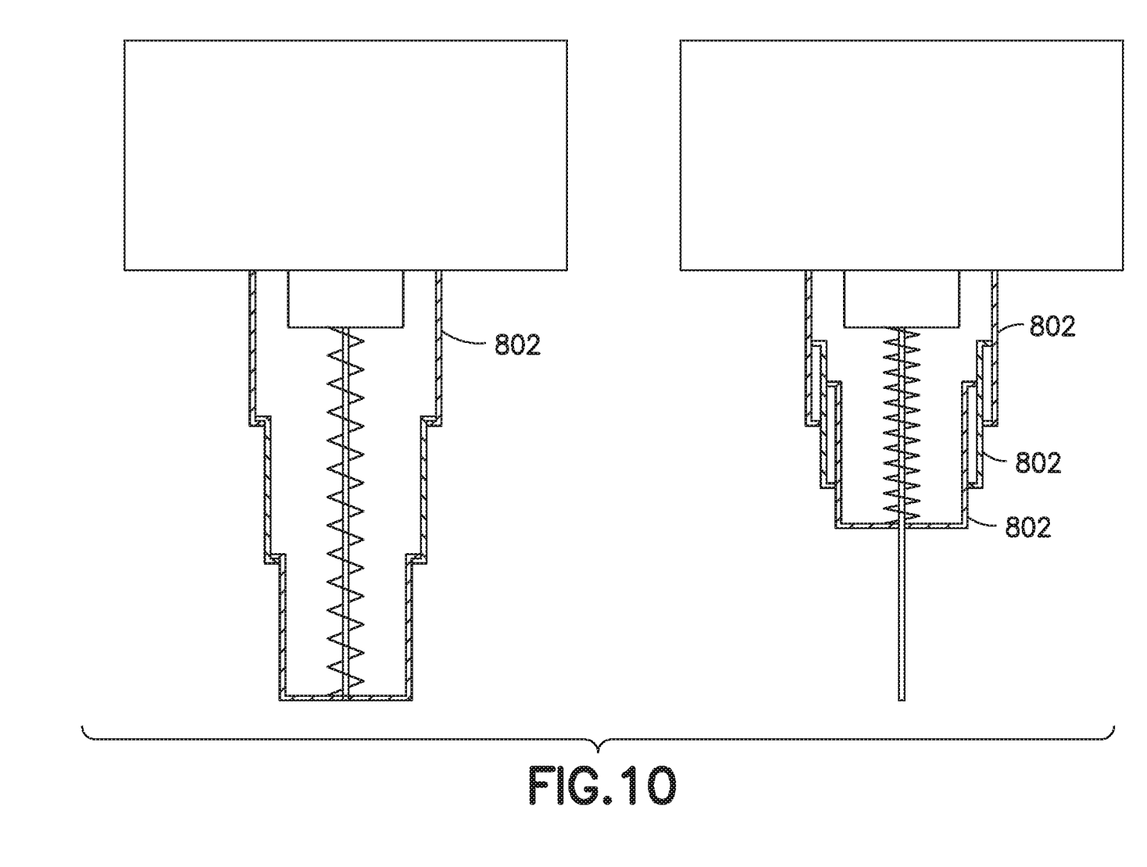
FIG. 10 is a cross-sectional view of the embodiment of FIG. 8.

Another needle shield embodiment 800 is illustrated in FIGS. 8-10. This embodiment 800 advantageously entirely encases the needle. Needle shield 800 comprises a series of nested sections 802 that are biased or spring loaded in the extended position. Upon insertion of the needle, the nested parts collapse to expose the needle, but remain pressed against the skin so that the needle remains unseen to the user. Upon withdrawal of the needle, the nested sections 802 extend again to encapsulate the needle. A side view of the nested sections are illustrated in FIG. 8 in a series of views ranging from fully extended to fully collapsed (needle inserted). FIG. 9 is a top elevation view of the needle shield 800. FIG. 9 is a cross sectional side view illustrating the needle shield 800 in the extended initial position, and in the collapsed position. The distal most section 802 is preferably connected to a spring or other biasing means so that the nested section 802 extend to the extended position as the needle is withdrawn.

Figure 11:
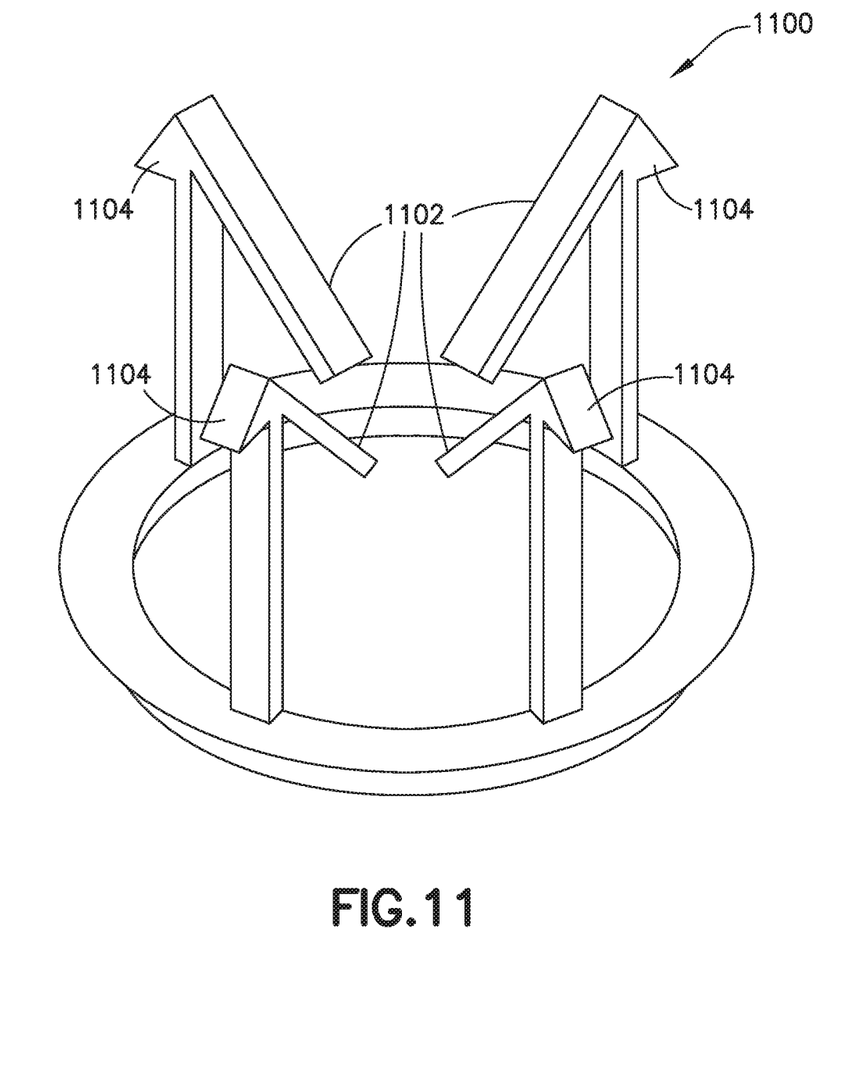
FIG. 11 illustrates a snap hook for use with a locking embodiment of the present invention.
Figure 12:
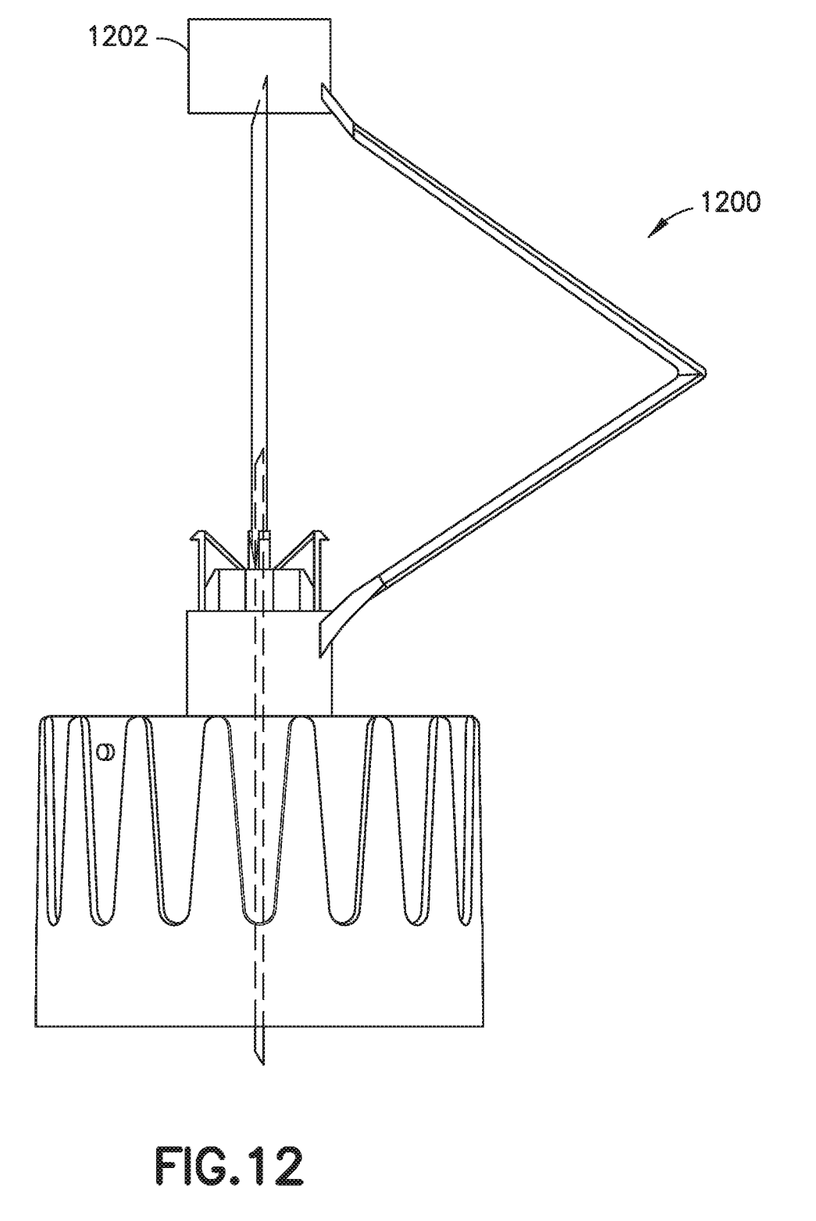
FIG. 12 illustrates a locking embodiment in a first configuration.
Figure 13:
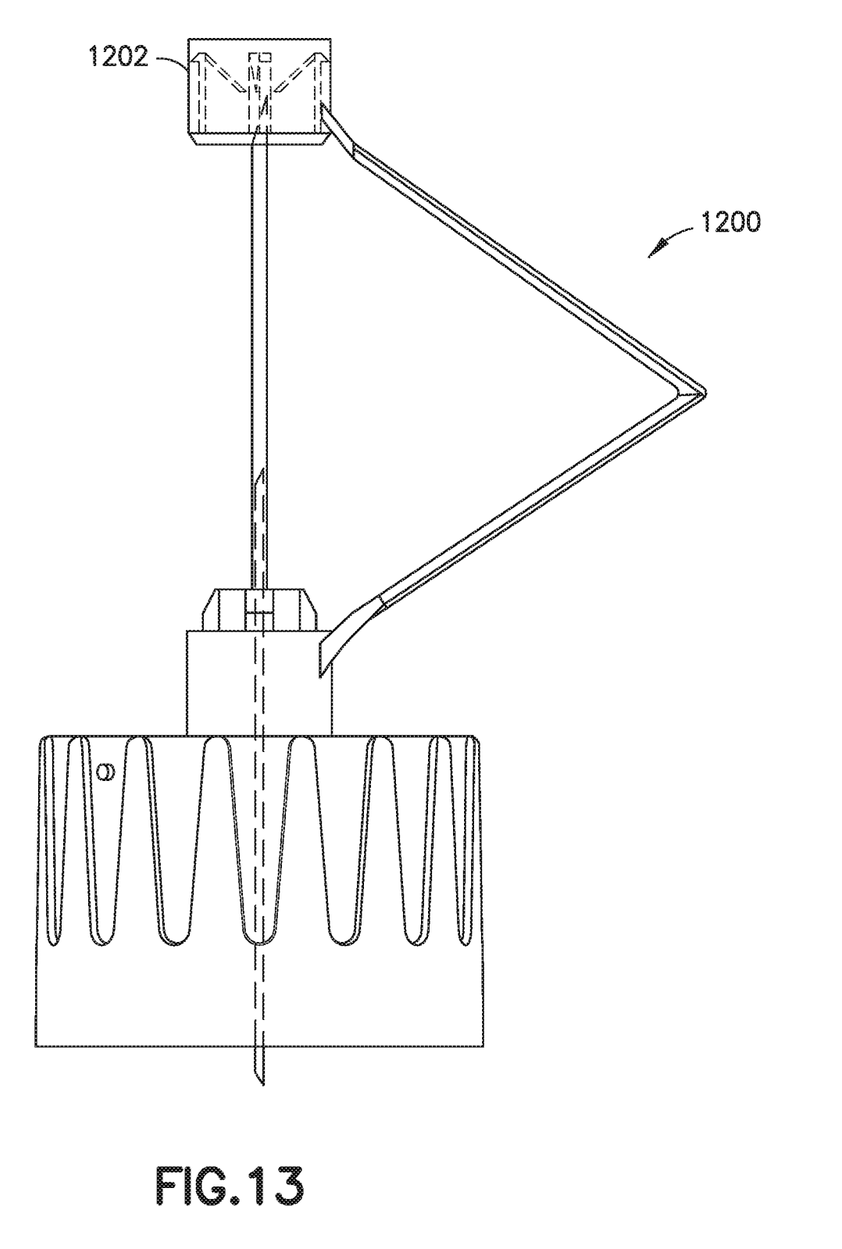
FIG. 13 illustrates a locking embodiment in a second configuration.

A locking mechanism for use with the needle shields described herein will now be described in connection with FIGS. 11-13. FIG. 11 illustrates a snap hook 1100 for use in a locking mechanism. The snap hook includes a plurality of barbs 1102 oriented to point inward and downward, leaving a space smaller than the gauge of the needle with which the locking mechanism will be used. FIG. 12 illustrates a needle shield 1200 incorporating a locking mechanism. As illustrated the snap hook 1100 is initially located at the proximal end of the needle. When the needle is used, the enclosure housing 1202 slides down the needle and engages the snap hook 1100. Tabs 1104 are provided on the snap hook 1100 to lock the snap hook into the enclosure housing 1202 the first time the needle is fully inserted, that is, the first time the enclosure housing 1202 slides all the way to the proximal end of the needle. Once the snap hook 1100 has locked into the enclosure housing 1202, and the needle is withdrawn, the enclosure housing 1202 returns to the distal end of the needle, and draws the snap hook 1100 with it. When Snap hook reaches the distal end of the needle, the barbs 1102 naturally flex inwards, and thus interfere with the needle if needle insertion is attempted again.

Figure 14:
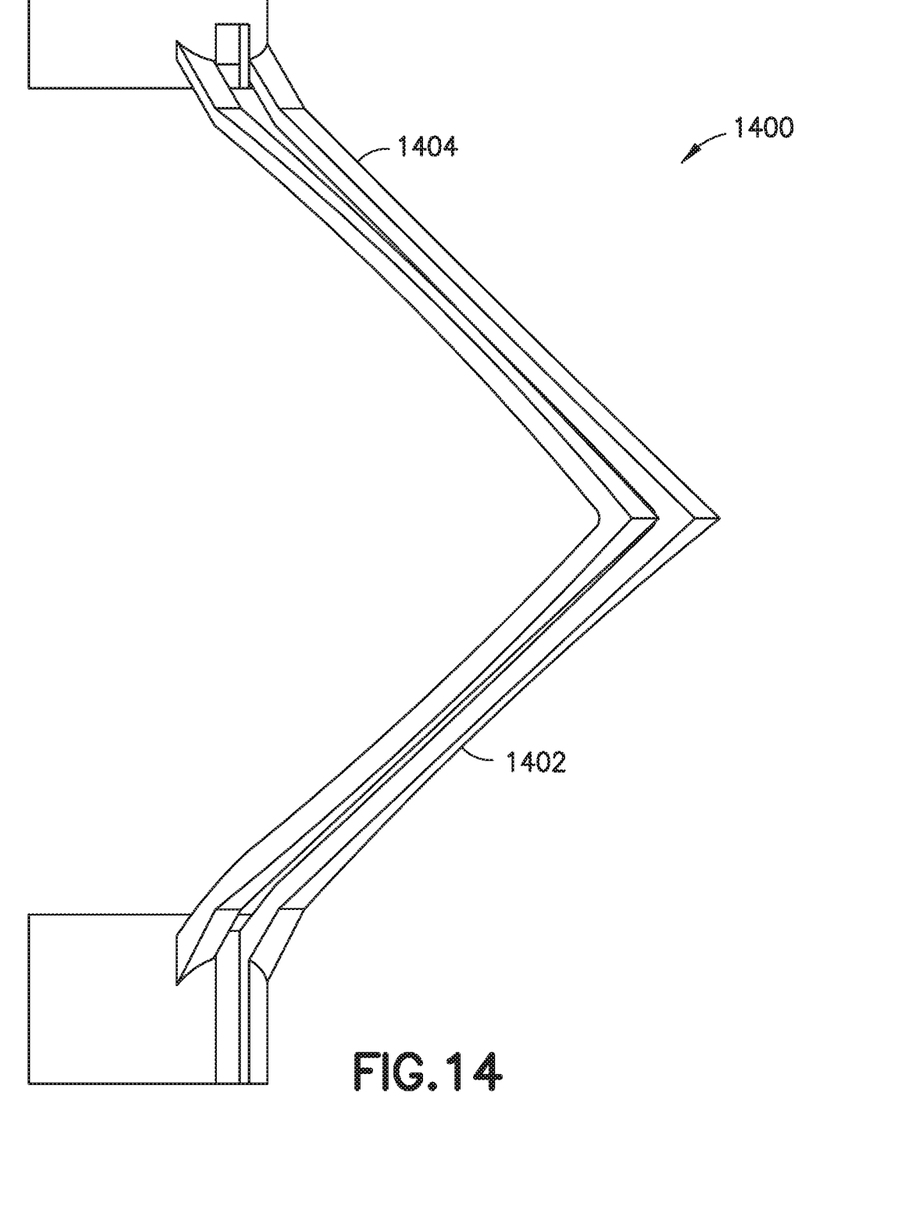
FIG. 14 illustrates a split-arm embodiment of the present invention.

FIG. 14 illustrates yet another embodiment of the needle shield 1400. In this embodiment the first 1402 and second 1404 arms are split to form two pairs of arms.

The above describe embodiments are intended to be illustrative of embodiments of the invention without being limiting. Those of ordinary skill in the art will readily appreciate that various changes and modifications to the embodiments described herein may be made without departing from the scope and spirit of the invention as described and illustrated herein.

What is claimed is:

1. A safety shield for a needle, comprising,
a base member fixed to a proximal end of a needle;
a first arm hinged to the base member and extending axially from the needle,
a second arm hinged to the first arm, the second arm also hinged to an enclosure housing movably connected to a portion of the needle distal to the proximal end of the needle, and slidable along the length of the needle, the enclosure housing adapted to contact the skin of a patient, and guide the needle into the patient during insertion of the needle into the patient; and
a locking mechanism to prevent the enclosure housing from sliding proximally from the distal end of the needle after a first use;
wherein the first and second arm bias the enclosure housing towards the distal end of the needle; and
wherein the locking mechanism comprises a snap hook member surrounding the needle and located adjacent to the base prior to first use, the snap hook further comprising a plurality of barbs oriented inwardly and proximally, and biased against the needle.

2. The safety shield of claim 1, wherein the safety shield is formed in a single shot molding process.

3. The safety shield of claim 1, wherein the safety shield comprises plastic.

4. The safety shield of claim 1, wherein the first arm is connected to the second arm via a bias housing that provides a biasing force to return the enclosure housing to the distal end of the needle.

5. The safety shield of claim 1, wherein the snap hook locks into the enclosure housing when the enclosure housing slides to the proximal end of the needle during first use.

6. The safety shield of claim 5, wherein the snap hook barbs flex to form an obstruction relative to the needle end when the snap hook barbs moves distally of the end of the needle during first use.

7. The safety shield of claim 1, wherein the safety shield comprises a plurality of first and second arms formed radially around the needle.

8. A safety shield for a needle, comprising,
   a base member fixed to a proximal end of a needle;
   a curved biasing arm formed as a single member that is curved and flexible along its entire length, connected to the base member and extending axially from the needle,
   the biasing arm also being connected at an opposite end to an enclosure housing movably connected to a portion of the needle distal to the proximal end of the needle, and slidable along the length of the needle, the enclosure housing adapted to contact the skin of a patient, and guide the needle into the patient during insertion of the needle into the patient;
   wherein the curved biasing arm biases the enclosure housing towards the distal end of the needle.

\* \* \* \* \*